United States Patent
Huang et al.

(10) Patent No.: US 12,006,501 B2
(45) Date of Patent: Jun. 11, 2024

(54) COMPOSITION OF DRUG TARGETS AND METHOD OF USING THEREOF

(71) Applicant: Shanghai Ninth People's Hospital, Shanghai Jiao Tong University School of Medicine, Shanghai (CN)

(72) Inventors: Xiaolu Huang, Shanghai (CN); Xiao Liang, Shanghai (CN); Qingfeng Li, Shanghai (CN); Bangda Chai, Shanghai (CN)

(73) Assignee: Shanghai Ninth People's Hospital, Shanghai Jiao Tong University School of Medicine, Shanghai (CN)

( * ) Notice: Subject to any disclaimer, the term of this patent is extended or adjusted under 35 U.S.C. 154(b) by 1081 days.

(21) Appl. No.: 16/759,362

(22) PCT Filed: Dec. 13, 2017

(86) PCT No.: PCT/CN2017/115764
§ 371 (c)(1),
(2) Date: Apr. 27, 2020

(87) PCT Pub. No.: WO2019/080284
PCT Pub. Date: May 2, 2019

(65) Prior Publication Data
US 2023/0193276 A1     Jun. 22, 2023

(30) Foreign Application Priority Data
Oct. 27, 2017   (CN) .......................... 201711022580.4

(51) Int. Cl.
*C12N 15/113* (2010.01)
*A61K 47/42* (2017.01)
*A61P 17/02* (2006.01)

(52) U.S. Cl.
CPC .......... *C12N 15/1137* (2013.01); *A61K 47/42* (2013.01); *A61P 17/02* (2018.01); *C12N 2310/14* (2013.01); *C12N 2320/32* (2013.01)

(58) Field of Classification Search
CPC .................. C12N 15/1137; C12N 2310/14; A61K 47/42; A61P 17/02
See application file for complete search history.

(56) References Cited

U.S. PATENT DOCUMENTS

2016/0068842 A1* 3/2016 Montgomery ....... C12N 15/113
                                                                435/375

FOREIGN PATENT DOCUMENTS

| CN | 102031260 | 4/2011 |
|---|---|---|
| CN | 103642800 | 3/2014 |
| CN | 106755395 | 5/2017 |

OTHER PUBLICATIONS

Zu and Gao, Non-viral Vectors in Gene Therapy: Recent Development, Challenges, and Prospects, 2021, The AAPS Journal, 23, 78, p. 1-12 (Year: 2021).*

(Continued)

*Primary Examiner* — J. E. Angell
*Assistant Examiner* — Keyur A Vyas
(74) *Attorney, Agent, or Firm* — JCIP GLOBAL INC.

(57) ABSTRACT

A composition of drug targets and the method of using thereof. The composition comprises a vector and a drug using FKBP10 and PCOLCE genes and/or the encoded proteins thereof as drug targets.

4 Claims, 5 Drawing Sheets
Specification includes a Sequence Listing.

(56) References Cited

OTHER PUBLICATIONS

Staab-Weijnitz et al., FK506-Binding Protein 10, a potential novel drug target for idiopathic pulmonary fibrosis, 2015, American J. of Respiratory Critical Care Med., 192, 455-467. (along with supplmental material). (Year: 2015).* www.genome.gov/genetics-glossary/Nucleotide (Year: 2023).*

"International Search Report (Form PCT/ISA/210) of PCT/CN2017/115764", mailed on Jul. 20, 2018, with English translation thereof, pp. 1-4.

Xiao Liang, et al., "Inhibition of FKBP10 Attenuates Hypertrophic Scarring through Suppressing Fibroblast Activity and Extracellular Matrix Deposition," Journal of Investigative Dermatology, vol. 137, Sep. 2017, pp. 2326-2335.

Victor W. Wong, et al., "Transcriptional Profiling of Rapamycin-Treated Fibroblasts From Hypertrophic and Keloid Scars," Ann Plast Surg., vol. 72, May 2016, pp. 1-19.

\* cited by examiner

SEQUENCE LISTING

<160> NUMBER OF SEQ ID NOS: 8

<210> SEQ ID NO 1
<211> LENGTH: 25
<212> TYPE: DNA
<213> ORGANISM: Artificial Sequence
<220> FEATURE:
<223> OTHER INFORMATION: Synthesized

<400> SEQUENCE: 1
gaaggaagau uaucauccu ccauu                                              25

<210> SEQ ID NO 2
<211> LENGTH: 25
<212> TYPE: DNA
<213> ORGANISM: Artificial Sequence
<220> FEATURE:
<223> OTHER INFORMATION: Synthesized

<400> SEQUENCE: 2
aauggaggga ugauaaucuu ccuuc                                             25

<210> SEQ ID NO 3
<211> LENGTH: 21
<212> TYPE: DNA
<213> ORGANISM: Artificial Sequence
<220> FEATURE:
<223> OTHER INFORMATION: Synthesized

<400> SEQUENCE: 3
ccacaccuac aauaccuaut t                                                 21

<210> SEQ ID NO 4
<211> LENGTH: 21
<212> TYPE: DNA
<213> ORGANISM: Artificial Sequence
<220> FEATURE:
<223> OTHER INFORMATION: Synthesized

<400> SEQUENCE: 4
auagguauug uagguguggt t                                                 21

<210> SEQ ID NO 5
<211> LENGTH: 19
<212> TYPE: DNA
<213> ORGANISM: Artificial Sequence
<220> FEATURE:
<223> OTHER INFORMATION: Synthesized

<400> SEQUENCE: 5
ccuuccucca gagagcuuu                                                    19

<210> SEQ ID NO 6
<211> LENGTH: 19
<212> TYPE: DNA
<213> ORGANISM: Artificial Sequence
<220> FEATURE:
<223> OTHER INFORMATION: Synthesized

<400> SEQUENCE: 6
ggaaggaggu cucucgaaa                                                    19

<210> SEQ ID NO 7
<211> LENGTH: 19
<212> TYPE: DNA
<213> ORGANISM: Artificial Sequence

```
<220> FEATURE:
<223> OTHER INFORMATION: Synthesized

<400> SEQUENCE: 7
ccuggcaacc aagugacuu                                                      19

<210> SEQ ID NO 8
<211> LENGTH: 19
<212> TYPE: DNA
<213> ORGANISM: Artificial Sequence
<220> FEATURE:
<223> OTHER INFORMATION: Synthesized

<400> SEQUENCE: 8
ggaccguugg uucacugaa                                                      19
```

COMPOSITION OF DRUG TARGETS AND METHOD OF USING THEREOF

CROSS-REFERENCE TO RELATED APPLICATION

This application is a 371 of international application of PCT application serial no. PCT/CN2017/115764, filed on Dec. 13, 2017, which claims the priority benefit of China application no. 201711022580.4, filed on Oct. 27, 2017. The entirety of each of the above mentioned patent applications is hereby incorporated by reference herein and made a part of this specification.

TECHNICAL FIELD

The present invention belongs to the field of biotechnology, and particularly relates to a composition of drug targets and use thereof.

BACKGROUND ART

Pathological scarring is a worldwide skin fibrosis disease. Its incidence varies among different populations. According to previous reports, the incidence of pathological scarring in white populations ranges from 5% to 37%, the incidence in patients after routine surgery ranges from 36% to 64%, and the incidence in deep burn patients can be as high as 91%. Pathological scarring is a fiber metabolic disease specific to human dermis caused by trauma inflammatory response and characterized by uncontrolled proliferation of fibroblasts (Fb) and excessive production and deposition of extracellular matrix (ECM) such as collagen. Its clinical manifestations are as follows: scar tissues higher than the normal surface of the skin within the wound area, significant congestion in the early phase, with or without pain or itching, and possible movement dysfunction if the disease occurs in the joint area. The indecent appearance and discomfort caused by pathological scarring put patients under tremendous pressure both physically and mentally. Hence, preventing scarring is not only a medical issue but also a social issue, and prevention and treatment of scarring especially poses a challenge to clinicians. At present, there are many methods for the treatment and prevention of pathological scarring. Most of them focus on striving to remove various factors leading to scar hyperplasia when epithelium covers the wound and the scar is not formed or in an "immature" stage, and preventing the scar from causing various deformities and dysfunctions to the body. Corticosteroids, tacrolimus, statins, tamoxifen, laser, radiation therapy, pressure prevention, and silicone product prevention, are used, but very limited effect on prevention and treatment have been achieved. Therefore, it is still of high academic and commercial value to searching for new treatments.

The pathogenesis of pathological scarring is still under research. The main pathogenic factors involved include abnormal metabolism of ECM, cytokines (such as TGF-β, platelet-derived growth factor and insulin-like growth factor), hypoxia and free radicals, genes level changes, etc., among which abnormal metabolism of ECM is the most primary pathogenic factor. Under normal circumstances, the synthesis and decomposition of ECM in human body is in a dynamic equilibrium, thereby maintaining relative stability. In the process of wound healing, if ECM synthesis increases markedly, pathological scarring or keloids will be formed. Therefore, inhibiting excessive deposition of collagen in ECM can be deemed as an important target for the prevention and treatment of pathological scarring.

FKBP10 is an immunophilin, belonging to the immunophilin FKBP subfamily. It is located on the protein of the rough endoplasmic reticulum in fibroblasts, serving as an enzyme in post-transcriptional modification of type I collagen. It may assist in folding the precursor collagen to form mature type I collagen, and is positive correlation to the secretion of type I collagen. In human body, FKBP10 mutation is closely associated with osteogenesis imperfect (OI). Patients deficient in FKBP10 cannot synthesize and secrete sufficient type I collagen in skin fibroblasts and bone tissues. As a result, the skin becomes weak and lack of elasticity, exhibiting a series of connective tissue-related symptoms such as easy fracture and difficulty in joint flexion. The expression of FKBP10 in human pathological scar is significantly higher than that in normal skin.

PCOLCE is an enzyme that may bind to type I precursor collagen, and cleave and modify it. After type I precursor collagen is cleaved by PCOLCE, its C-terminal protease activity significantly increases. Then, the N-terminus and C-terminus are cleaved. Finally, the collagen goes through trimerization reaction to be polymerized into mature collagen fibers. PCOLCE is closely associated with the degradation of extracellular matrix, and its expression in hypertrophic scar is significantly higher than that in normal skin.

The current methods for prevention and treatment of pathological scarring have the following limitations: surgical therapy results in a high recurrence rate of the disease and is not suitable for patients with large areas of scars; compression therapy and silica gel therapy are effective for extensively burned patients, but only useful for early prevention, and limited in effect for the treatment of scars that have been formed; radiation therapy has certain radiation damage to the patient's whole body and local areas; cryotherapy is only suitable for small areas of scars, and the treatment may cause complications such as deeper skin pigmentation and mild skin atrophy; glucocorticoid treatment may generate complications such as skin atrophy, depigmentation, telangiectasia, women's menstrual disorders, and ulceration or calcification at the injection site; laser therapy has low clinical efficacy, and may induce new scars; antitumor drug treatment negatively impacts normal cell metabolism, and its clinical values are still unclear; tacrolimus, statins, tamoxifen and other drugs have limited clinical efficacy, and their therapeutic targets are still unclear.

SUMMARY OF THE INVENTION

The present invention intends to solve the technical problem of providing a composition of drug targets and the use thereof. The composition achieves the effect of treating fibrosis-related diseases by interfering with FKBP10 and PCOLCE to inhibit the formation of tissue fibrosis, and to inhibit biological behaviors such as proliferation, differentiation, anti-apoptosis, and secretion of a large amount of extracellular matrix, etc. of skin fibroblasts.

The composition of drug targets according to the present invention comprises a vector, and a drug using FKBP10 and PCOLCE genes and/or the encoded proteins thereof as drug targets.

The drug using FKBP10 and PCOLCE genes and/or the encoded proteins thereof as drug targets is an inhibitor for FKBP10 and PCOLCE genes and/or the encoded proteins thereof.

The drug using FKBP10 and PCOLCE genes and/or the encoded proteins thereof as drug targets includes, but is not limited to, a neutralizing antibody, a small molecule drug, a small nucleotide, a microRNA, an antisense molecule or a polypeptide for interfering with the expression and function of FKBP10 and PCOLCE genes and/or the encoded proteins thereof.

The interfering modes comprises simultaneously interfering with KBP10 and PCOLCE genes and/or the encoded proteins thereof, or first interfering with KBP10 gene and/or the encoded protein thereof and then interfering with PCOLCE gene and/or the encoded protein thereof.

The drug using FKBP10 and PCOLCE genes and/or the encoded proteins thereof as drug targets is administered by local injection or smearing.

The vector includes, but is not limited to, a histidine polypeptide, a lysine polypeptide, a branched histidine-lysine copolymer polypeptide, a cationic polymer, silicon nanoparticles, a lipid vector or a viral vector. Other pharmaceutically acceptable vectors may be used as well.

The method of using the composition of drug targets according to the present invention, characterized in that the composition is used for preparing a medicament for treating fibrosis-related diseases.

BENEFICIAL EFFECTS (1) The present invention achieves the effect of treating fibrosis-related diseases, for example, pathological scarring by interfering with FKBP10 and PCOLCE to inhibit the formation of tissue fibrosis, and to inhibit biological behaviors such as proliferation, differentiation, anti-apoptosis, and secretion of a large amount of extracellular matrix, etc. of skin fibroblasts.

(2) Compared with drugs such as tacrolimus, statins and tamoxifen, the drug involved in the present invention has clear therapeutic targets, and avoid defects such as unclear therapeutic mechanism, low efficiency and tendency to cause side effects.

(3) Compared with hormonal drugs like corticosteroids, the drug involved in the present invention circumvents a series of side effects that may be brought by the use of hormonal drugs.

(4) Compared with antitumor drugs and radiation therapy, the drug involved in the present invention is unlikely to damage normal cells in human body.

(5) Compared with laser therapy, the drug involved in the present invention avoids the defect of superficial treatment and is unlikely to induce new scars.

(6) Compared with surgery and cryotherapy, the drug involved in the present invention may be useful for treatment of large areas of pathological scars, overcoming the defect of treatment in a small range.

(7) Compared with compression therapy and silica gel therapy, the drug involved in the present invention is useful for treatment after pathological scars have been formed, breaking through the limitation of early prevention.

(8) The drug involved in the present invention has a remarkable advantage in costs, i.e. low costs of synthesis, over the currently available drugs.

DETAILED DESCRIPTION OF THE INVENTION

The present invention is further described below in conjunction with specific Examples. It should be understood that these Examples are only used to illustrate the present invention rather than to limit the scope of the present invention. In addition, it should be understood that, after reading the content taught by the present invention, persons skilled in the art can make various changes or modifications to the present invention, and these equivalents also fall within the scope defined by the appended claims of the present application.

There are many ways to interfere with the expression and function of FKBP10 and PCOLCE genes and/or the encoded proteins thereof, for example, using a neutralizing antibody, a small molecule drug, a small nucleotide, a microRNA, or a polypeptide. Taking a small nucleotide drug as an example and human hypertrophic scar fibroblasts (HHSF) as target cells, the Examples demonstrate that interfering with FKBP10 and PCOLCE expression can inhibit the activity of HHSF, and decrease the expression of fibrosis-related markers. In addition, by establishing mouse hypertrophic scar models and injecting a small nucleotide into local skin, it has been verified that interfering with FKBP10 and PCOLCE can inhibit the formation of mouse hypertrophic scars.

Example 1

1. Experimental Materials 1.1 Small Nucleotide Sequence

Small nucleotide (Small interfering RNA, siRNA): It is a small RNA molecule (~21-25 nucleotides) processed by Dicer (an enzyme specific for double-stranded RNA in the RNAase III family). SiRNA is a main member of siRISC, which stimulates silencing of the complementary target mRNA. RNA interference (RNAinterference, RNAi) refers to specific degradation of intracellular mRNA mediated by endogenous or exogenous double-stranded RNA (dsRNA), which leads to silencing of the expression of the target gene and loss of corresponding functional phenotype.

Its (the small interfering RNA) sequence for human FKBP10 mRNA:

```
Sense strand (SEQ ID NO. 1):
5'-GAAGGAAGAUUAUCAUCCCUCCAUU-3';

Antisense strand (SEQ ID NO. 2):
5'-AAUGGAGGGAUGAUAAUCUUCCUUC-3';
```

Its (the small interfering RNA) sequence for mouse FKBP10 mRNA:

```
Sense strand:
                                    (SEQ ID NO. 3)
5'-CCACACCUACAAUACCUAUTT-3';

Antisense strand:
                                    (SEQ ID NO. 4)
5'-AUAGGUAUUGUAGGUGUGGTT-3';
```

Its (the small interfering RNA) sequence for human PCOLCE mRNA:

```
Sense strand:
                                    (SEQ ID NO. 5)
5'-CCUUCCUCCAGAGAGCUUU-3';

Antisense strand:
                                    (SEQ ID NO. 6)
5'-GGAAGGAGGUCUCUCGAAA-3';
```

Its (the small interfering RNA) sequence for mouse PCOLCE mRNA:

```
Sense strand:
                                    (SEQ ID NO. 7)
5'-CCUGGCAACCAAGUGACUU' ;

Antisense strand:
                                    (SEQ ID NO. 8)
5'-GGACCGUUGGUUCACUGAA-3'.
```

1.2 Method for Formulating a Solution of Small Nucleotide/Histidine-Lysine Polymer (HKP) Nanoparticles/Methyl Cellulose The histidine-lysine polymer (HKP), which is used as a vector for siRNA transfection, has a lysine skeleton, including a branched chain containing multiple histidine, lysine or aspartic acid. HKP was dissolved in DEPC-treated water to form a DEPC aqueous solution. Then the DEPC aqueous solution was mixed with a siRNA (purchased from Shanghai Jima Pharmaceutical Technology Co., Ltd.) aqueous solution at a mass ratio of 4:1 and a volume ratio of 1:1 to form nanoparticles having an average diameter of 150-200 nm. The resulting HKP-siRNA aqueous solution was translucent without any obvious sediment aggregation, and could be stored at 4° C. for at least three months.

1.3 Method for Formulating Small Nucleotide Injections

Formulation of small nucleotide injections for in vivo experiments: Specially modified siRNA (purchased from Ruibo Biotechnology Co., Ltd.) and HKP were dissolved with a DEPC-5% glucose solution to prepare siRNA and HKP aqueous solutions, respectively. Then, the HKP aqueous solution was mixed with the siRNA aqueous solution at a mass ratio of 4:1 and a volume ratio of 1:1 to form nanoparticles having an average diameter of 150-200 nm. The resulting HKP-siRNA aqueous solution was translucent without any obvious sediment aggregation, and could be stored at 4° C. for at least three months.

2. Experimental Methods 2.1 Extraction and Cultivation of Human Fibroblasts

Clinical specimens (human hypertrophic scars, keloids or normal skin) were soaked with Dispase II (2 mg/ml, Life Technologies, ThermoFisher) overnight at 4° C., before they were peeled and removed of the epidermis. The tissues were minced in a sterile environment, soaked with 4 mg/ml collagenase, and digested with a shaker at 37° C. for 2-4 hours. The cell suspension was filtered with a filter screen, and centrifuged at 1500 rpm for 5 min to remove the supernatant. The cell sediments were re-suspended in a culture medium, and then inoculated to a DMEM medium. This medium was changed every 2 days for routine cultivation.

2.2 Establishment of Mouse Hypertrophic Scar Models 12-week-old C57/BL6 mice were anesthetized to perform a longitudinal incision of 1 cm on their back skin, under which micro-permeable capsules (Alzet Model 1004; Durect Corp., Cupertino, CA, USA) filled with a Bleomycin solution (2.8 mg/ml) were embedded, and the incision was sutured. After 56 days, the mice were euthanized and sampled.

2.3 Small Nucleotide Injections

On the first day when scars were formed on the mice, small nucleotide injections through intradermal injection was started. The mice in the control group, FKBP10 siRNA alone administration group, and PCOLCE siRNA alone administration group were injected once every 3 days until sampling on the 56th day of model establishment. As for the FKBP10 siRNA+PCOLCE siRNA simultaneous administration group, the formulated injections have a final FKBP10 siRNA concentration of 200 μg/ml, and a final PCOLCE siRNA concentration of 50 μg/ml, and each of these two drugs was combined with HKP to prepare HKP-siRNA solutions for mixed injection once every 3 days until sampling on the 56th day of model establishment. As for the FKBP10 siRNA+(24 h) PCOLCE siRNA administration group, FKBP10 siRNA (200 μg/ml) was injected on the first day, PCOLCE siRNA (50 μg/ml) was injected 24 hours later, and the two drugs were alternately injected every 3 days until sampling on the 56th day of model establishment.

2.4 siRNA Transfection of In Vitro Cultured Cells

When the cell density reached about 70%, the medium in which the cells were cultivated was changed, and added with the HKP-siRNA aqueous solution (refer to Section 1.2 for the method). For the cells in the control group, FKBP10 siRNA alone administration group, and PCOLCE siRNA alone administration group, the final siRNA concentration in the culture medium is 50 nM, and the cells were tested after 24 hours of cultivation. For the cells in the FKBP10 siRNA+PCOLCE siRNA simultaneous interfering group, the final FKBP10 siRNA concentration in the culture medium is 50 nM and the final PCOLCE siRNA concentration in the culture medium is 25 nM. Each of FKBP10 siRNA and PCOLCE siRNA was combined with HKP to prepare HKP-siRNA solutions before they were mixed in the culture medium. The cells were tested after 24 hours of cultivation. For the cells in the FKBP10 siRNA+(24 h) PCOLCE siRNA interfering group, the cells were first cultivated in a culture medium with a final FKBP10siRNA concentration of 50 nM, then 24 hours later changed to be cultivated in a culture medium with a final PCOLCE siRNA concentration of 50 nM, and later tested after 24 hours of cultivation.

2.5 Real-Time Quantitative PCR

Total RNA of tissues or cells was extracted by Trizol (Invitrogen, Grand Island, NY, USA), and RNA concentration and purity were measured by ultraviolet spectrophotometry (ND-1000, Thermo, Rockford, IL, USA). The extracted total RNA was subjected to reverse transcription reaction by means of a RT-PCR kit (TaKaRa, Shiga, Japan) and ABI HT7900 PCR instrument (Applied Biosystems, Foster City, CA, USA) to synthesize cDNA. The above cDNA served as a template for real-time quantitative PCR.

In a 20 μl reaction system:
MIX (SYBR Premix Ex Taq): 10 μl;
Upstream primer: 0.4 μl;
Downstream primer: 0.4 μl;
ROX II: 0.4 μl;
cDNA: 2 μl;
Deionized water: 6.8 μl.

Each reaction tube was prepared, briefly centrifuged to mix evenly, and then placed in a PCR reactor (Applied Biosystems). Reaction conditions: after hot start at 95° C. for 10 seconds, running the process for 40 cycles as 95° C. for 15 seconds, 60° C. for 30 minutes, 72° C. for 3 minutes. When the reaction was completed, the results were analyzed with an analysis software using ΔΔCT Relative Quantitation method. Each sample was configured with three parallel wells, and the GADPH primer served as an internal control.

2.6 Immunohistochemistry/Fluorescence Staining

Clinical specimens and animal tissues were sampled, routinely fixed, dehydrated, and embedded in paraffin, and prepared into 6 μm sections. After dewaxing, these sections were blocked with 1% sheep serum, and incubated with primary antibodies at 4° C. overnight. Then the sections were washed with BSA, and incubated with secondary antibodies comprising horseradish peroxidase or labeled with fluorescence at 37° C. for 2 hours. Colors were developed and pictures were taken.

2.7 Detection of CCK-8 Cell Activity

The proliferation activity of cells cultivated in vitro was tested by means of the CCK-8 method. The CCK-8 kit was purchased from Dojindo (Tokyo, Japan), and the experimental procedures were carried out in strict accordance with the kit instructions.

Figure 1:
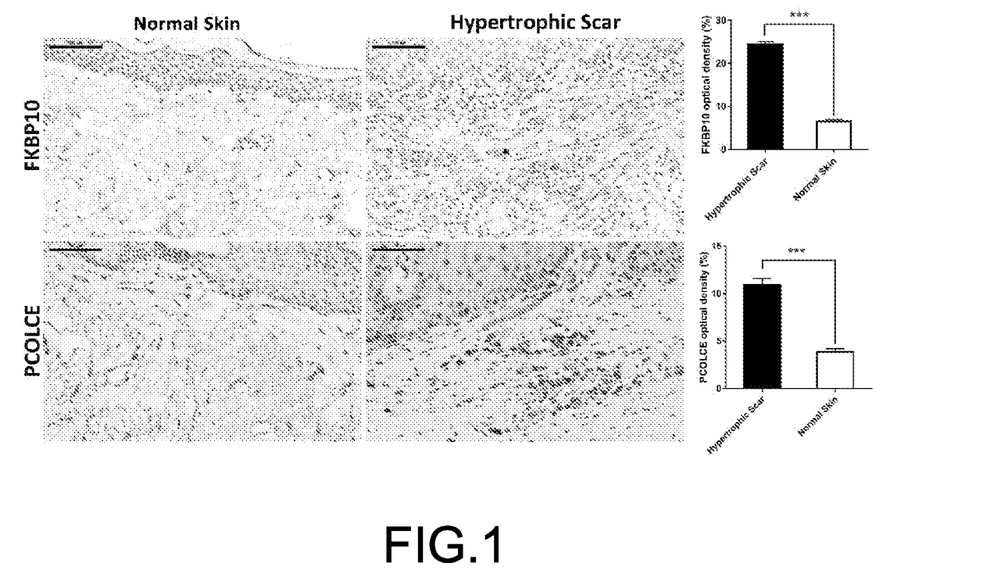
FIG. 1 shows a comparison of differences between FKBP10 and PCOLCE expression in human hypertrophic scar and normal skin.

3. Experimental Results 3.1 Comparison of Differences Between FKBP10 and PCOLCE Expression in Human Hypertrophic Scar and Normal Skin Clinical samples (human hypertrophic scar and normal skin) were subjected to immunohistochemical detection. The immunohistochemical results showed that the expressions of FKBP10 and PCOLCE in human hypertrophic scars were significantly higher than those in normal skin ($p<0.001$) (FIG. 1).

Figure 2:
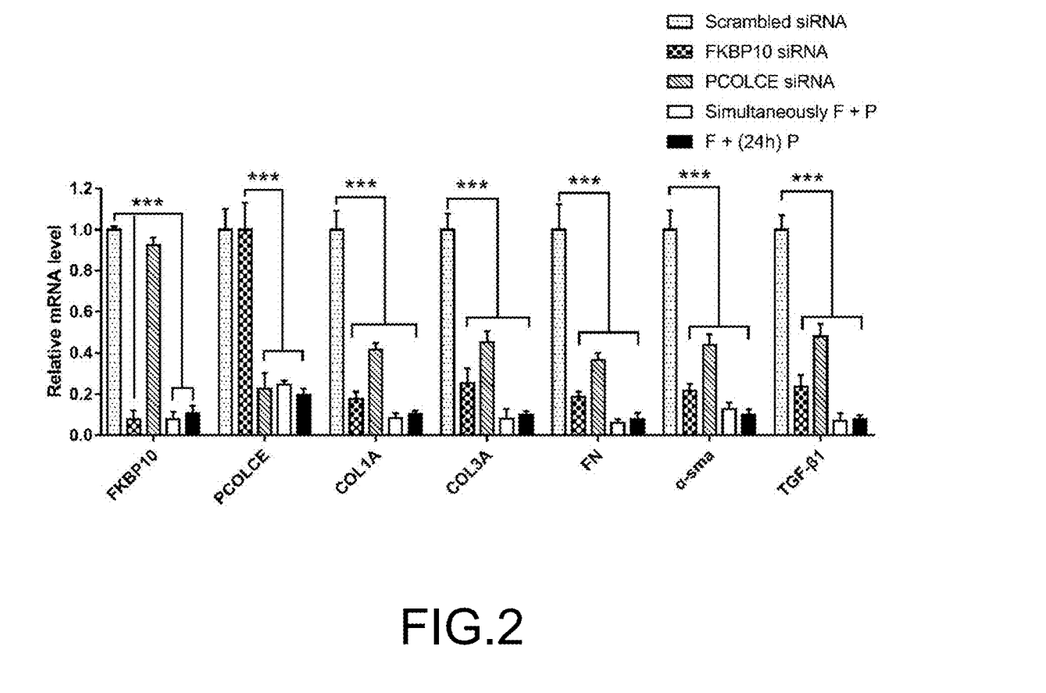
FIG. 2 shows knock downing FKBP10 and/or PCOLCE expression can inhibit the expression of fibrosis markers in human hypertrophic scar fibroblasts; COL1A is collagen type I alpha 1, COL3A is collagen type III alpha 1, FN is fibronectin, α-sma is alpha smooth muscle Actin, TGF-β1 is transforming growth factor beta 1.

3.2 Knocking Down FKBP10 and/or PCOLCE Expression can Inhibit the Expression of Fibrosis Markers in Human Hypertrophic Scar Fibroblasts Human hypertrophic scar fibroblasts were isolated and cultivated, in which FKBP10 and/or PCOLCE were knocked down by means of RNAi technology, and the mRNA levels of fibrosis markers COL1A, COL3A, FN, α-SMA and TGF-β1 MRNA were detected by real-time quantitative PCR (q-PCR). The q-PCR results showed that knocking down FKBP10 and/or PCOLCE could significantly reduce the expression of fibrosis markers COL1A, COL3A, FN, α-SMA and TGF-β1 ($p<0.001$). Among them, the cells treated by two methods, namely, simultaneously interfering with two targets FKBP10 and PCOLCE, and first interfering with FKBP10 target and 24 hours later interfering with PCOLCE target, had lower expression of fibrosis markers than the cells in the group where FKBP10 or PCOLCE was interfered with alone. In other words, interfering with dual targets of FKBP10 and PCOLCE achieved better effect than interfering with one of the two targets alone (FIG. 2).

Figure 3:
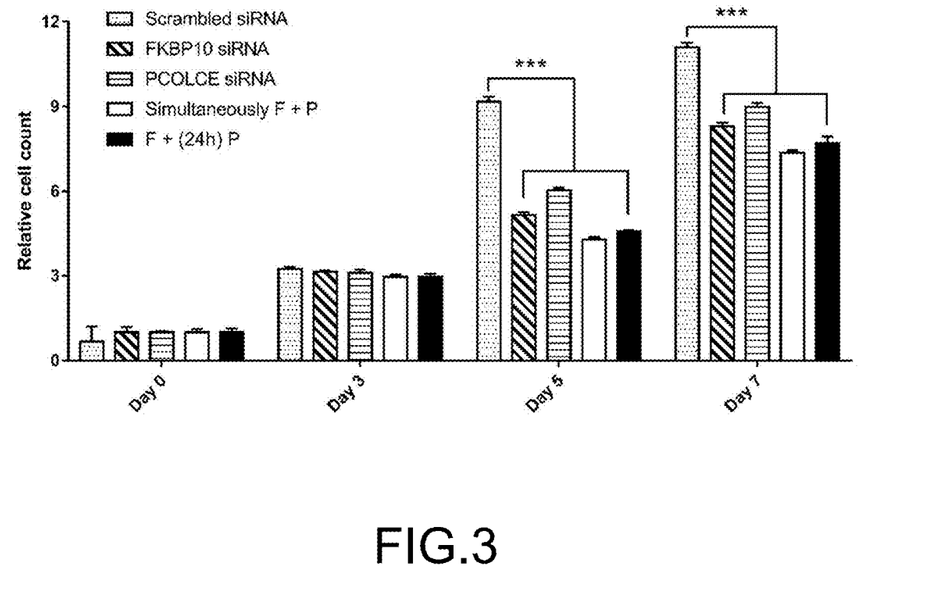
FIG. 3 shows interfering with human FKBP10 and/or PCOLCE using a small nucleotide can inhibit the activity of human hypertrophic scar fibroblasts.

3.3 Interfering with Human FKBP10 and/or PCOLCE Using a Small Nucleotide can Inhibit the Activity of Human Hypertrophic Scar Fibroblasts Human hypertrophic scar fibroblasts were isolated and cultivated, in which the expression of FKBP10 and/or PCOLCE was interfered with using a small nucleotide. The proliferation activity of human hypertrophic scar fibroblasts was detected by means of the CCK-8 method. The results showed that after interfering for 5d and 7d, the proliferation activity of the cells with FKBP10 and/or PCOLCE knocked down was significantly lower than that in the control group. Meanwhile, the cells treated by two methods, namely, simultaneously interfering with two targets FKBP10 and PCOLCE, and first interfering with FKBP10 target and 24 hours later interfering with PCOLCE target, had lower proliferation activity than the cells in the group where FKBP10 or PCOLCE was interfered with alone. In other words, interfering with dual targets of FKBP10 and PCOLCE achieved better effect than interfering with one of the two targets alone (FIG. 3).

Figure 4:
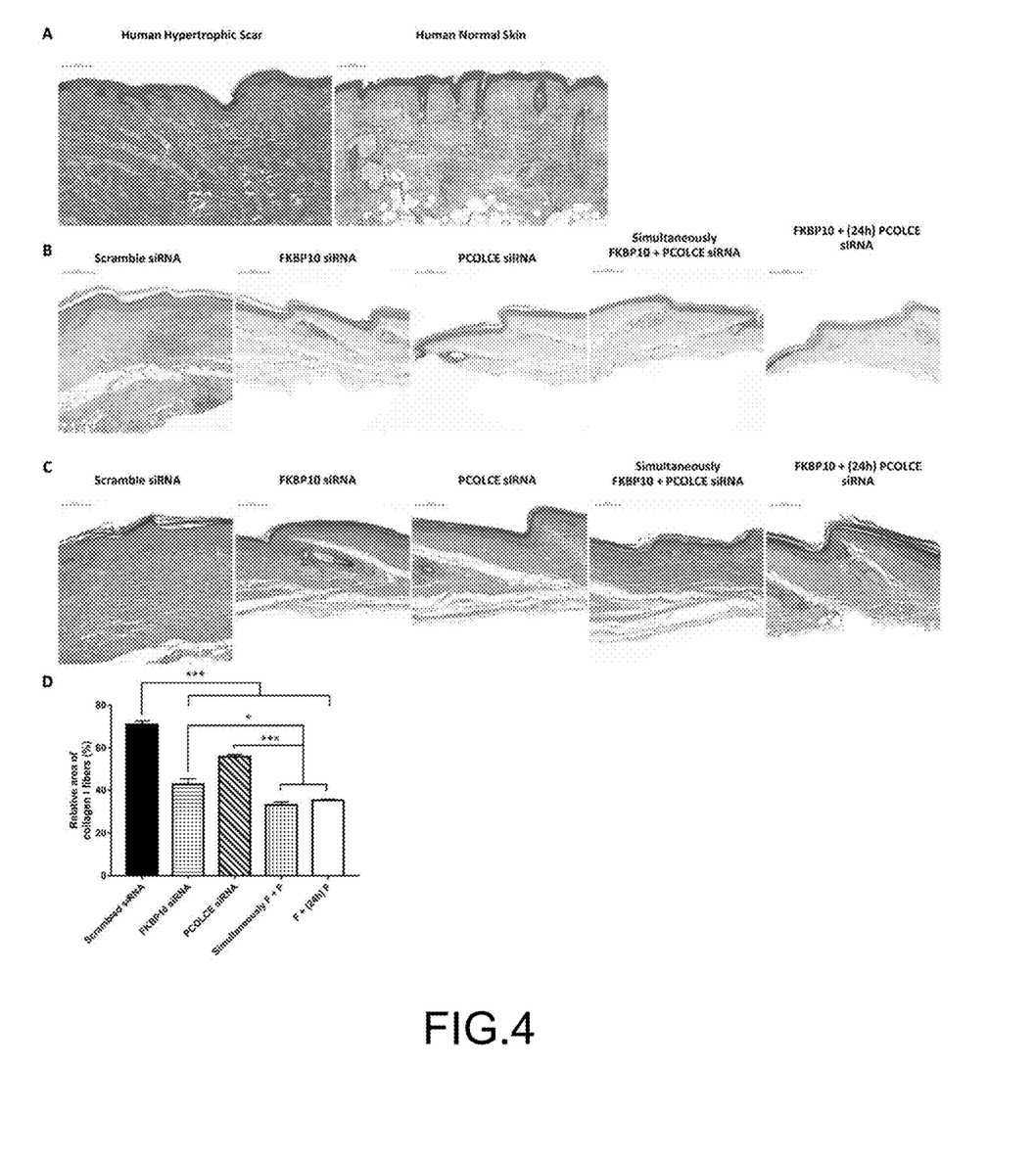
FIG. 4 shows interfering with mouse FKBP10 and/or PCOLCE using a small nucleotide can inhibit the formation of mouse hypertrophic scars; wherein, A of FIG. 4: HE staining of human hypertrophic scar and normal skin; B of FIG. 4: HE staining of mouse models in various interfering modes; C of FIG. 4: Masson staining of mouse models in various interfering modes; D of FIG. 4: a statistic diagram of collagen content in Masson stained mouse models.

3.4 Interfering with Mouse FKBP10 and/or PCOLCE Using a Small Nucleotide can Inhibit the Formation of Mouse Hypertrophic Scars Classic mouse hyperplastic scar models were established to simulate pathological changes of human hypertrophic scar (A of FIG. 4 to C of FIG. 4). HE and Masson staining were performed on the sampled mouse scars. The results showed that after interfering with FKBP10 and/or PCOLCE, the characteristics of skin hypertrophic scars (these characteristics include: thickening of epidermis and dermis, reduction of skin accessory organs, increased collagen and disordered arrangement, etc.) were significantly suppressed ($p<0.001$). Among them, the two methods, namely, simultaneously interfering with two targets FKBP10 and PCOLCE, and first interfering with FKBP10 target and 24 hours later interfering with PCOLCE target, achieved significantly better effect than interfering with FKBP10 or PCOLCE alone ($p<0.05$).

Figure 5:
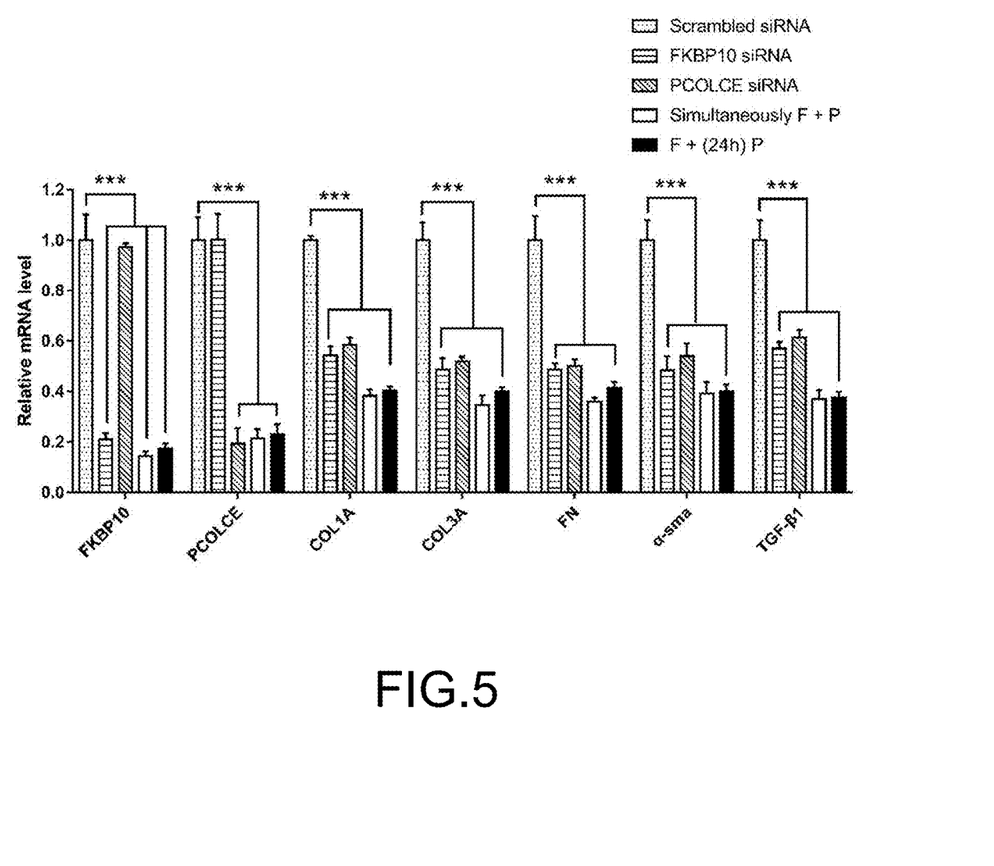
FIG. 5 shows interfering with mouse FKBP10 and/or PCOLCE using a small nucleotide can inhibit the expression of fibrosis markers in mice's skin. COL1A is collagen type I alpha 1, COL3A is collagen type III alpha 1, FN is fibronectin, α-sma is alpha smooth muscle Actin, TGF-β1 is transforming growth factor beta 1.

3.5 Interfering with Mouse FKBP10 and/or PCOLCE Using a Small Nucleotide can Inhibit the Expression of Fibrosis Markers in Mice's Skin A small nucleotide was used to interfere with the expression of FKBP10 and/or PCOLCE in the mouse model, and the skin samples were subjected to q-PCR detection. The results showed that interfering with FKBP10 and/or PCOLCE could significantly reduce the expression of collagen I, collagen III, fibronectin, α-SMA and TGF-β1 ($p<0.001$). Among them, the skin treated by the two methods, namely, simultaneously interfering with two targets FKBP10 and PCOLCE, and first interfering with FKBP10 target and 24 hours later interfering with PCOLCE target, had lower expression of fibrosis markers than the skin in the group where FKBP10 or PCOLCE was interfered with alone. In other words, interfering with dual targets of FKBP10 and PCOLCE achieved better effect than interfering with one of the two targets alone (FIG. 5).

What is claimed is:

1. A drug combination comprising siRNAs that target human or mouse FK506 binding protein 10 (FKBP10) and siRNAs that target human or mouse procollagen C-endopeptidase enhancer (PCOLCE) transcript,
wherein sequence of the siRNA for human FKBP10 mRNA are as follows:
sense strand: SEQ ID NO: 1, 5'-GAAGGAAGAUUAU-CAUCCCUCCAUU-3';
antisense strand: SEQ ID NO: 2, 5'-AAUGGAGG-GAUGAUAAUCUUCCUUC-3';
wherein sequence of the siRNA for mouse FKBP10 mRNA are as follows:
sense strand: SEQ ID NO: 3, 5'-CCACACCUA-CAAUACCUAUTT-3';
antisense strand: SEQ ID NO: 4, 5'-AUAGGUAUU-GUAGGUGUGGTT-3';
wherein sequence of the siRNA for human PCOLCE mRNA are as follows:
sense strand: SEQ ID NO: 5, 5'-CCUUC-CUCCAGAGAGCUUU-3';
antisense strand: SEQ ID NO: 6, 5'-AAAGCUCUCUG-GAGGAAGG-3';
wherein sequence of the siRNA for mouse PCOLCE mRNA are as follows:
sense strand: SEQ ID NO: 7, 5'-CCUGGCAAC-CAAGUGACUU-3';
antisense strand: SEQ ID NO: 8, 5'-AAGUCACUUG-GUUGCCAGG-3'.

2. A method of administering the drug combination according to claim 1, wherein the drug combination is administered by local injection or smearing.

3. The drug combination according to claim 1 comprising a vector, wherein the vector is a histidine polypeptide, a lysine polypeptide, or a branched histidine-lysine copolymer polypeptide.

4. A method of treating hyperplastic pathological scar comprising administering the drug combination according to claim 1.

* * * * *